(12) United States Patent
Doynov et al.

(10) Patent No.: US 6,922,238 B2
(45) Date of Patent: Jul. 26, 2005

(54) SELF-TUNING PULSE FLAME PHOTOMETRIC DETECTOR SYSTEM AND ASSOCIATED METHOD OF SELF-TUNING

(75) Inventors: Plamen G. Doynov, Kansas City, MO (US); Douglas C. Stewart, Mission, KS (US); Keith D. Wilson, Lees Summit, MO (US)

(73) Assignee: Midwest Research Institute, Inc., Kansas City, MO (US)

( * ) Notice: Subject to any disclaimer, the term of this patent is extended or adjusted under 35 U.S.C. 154(b) by 365 days.

(21) Appl. No.: 10/248,494

(22) Filed: Jan. 23, 2003

(65) Prior Publication Data

US 2004/0145736 A1 Jul. 29, 2004

(51) Int. Cl.[7] .......................... G01J 3/30; G01N 30/02; G01N 30/04
(52) U.S. Cl. ...................... 356/315; 356/417; 73/23.35; 73/23.41; 96/101
(58) Field of Search ................................ 356/315, 417; 73/23.35, 23.22, 23.24, 23.41; 96/101–107

(56) References Cited

U.S. PATENT DOCUMENTS

| | | | |
|---|---|---|---|
| 5,153,673 A | 10/1992 | Amirav | |
| 5,268,302 A | 12/1993 | Rounbehler et al. | |
| 5,465,607 A | 11/1995 | Corrigan et al. | |
| 5,547,497 A | 8/1996 | Klemp et al. | |
| 5,611,846 A | 3/1997 | Overton et al. | |
| 5,686,656 A | 11/1997 | Amirav et al. | |
| 5,741,711 A | 4/1998 | Amirav et al. | |
| 5,780,717 A | 7/1998 | Wise et al. | |
| 5,808,178 A | 9/1998 | Rounbehler et al. | |
| 5,929,321 A | 7/1999 | Bertrand | |
| 5,987,959 A | 11/1999 | Klee et al. | |
| 6,131,440 A | 10/2000 | Bertrand | |
| 6,386,014 B1 | 5/2002 | Butch | |
| 6,519,030 B1 * | 2/2003 | Norman et al. | ............. 356/315 |

* cited by examiner

Primary Examiner—Layla Lauchman
(74) Attorney, Agent, or Firm—Blackwell Sanders Peper Martin LLP

(57) ABSTRACT

A system and method for tuning a pulsed-flame photometric detector including providing a carrier gas within a predetermined gas flow range to the pulsed-flame photometric detector, providing at least one combustible fuel to the pulsed-flame photometric detector, applying voltage to an igniter coil associated with the pulsed-flame photometric detector, verifying that the pulsed-flame photometric detector is pulsing above a lower predetermined frequency and above a higher predetermined frequency, adjusting the gas flow of the at least one combustible fuel to the pulsed-flame photometric detector so that at least one cycle of ignition, propagation and then termination is present, heating a container to a predetermined temperature, allowing the at least one carrier gas to flow within the container, housing a tuning compound, and monitoring a width of a sulfur emission resulting from the combustion of the tuning compound to evaluate the width of sulfur emission signal all through a controller.

36 Claims, 12 Drawing Sheets

SELF-TUNING PULSE FLAME PHOTOMETRIC DETECTOR SYSTEM AND ASSOCIATED METHOD OF SELF-TUNING

The U.S. Government has a paid-up license in this invention and the right in limited circumstances to require the patent owner to license others on reasonable terms as provided for by the terms of Contract No. DSWA01-98-D-0126 awarded by the Defense Threat Reduction Agency.

BACKGROUND OF INVENTION

The operation of a pulsed-flame photometric detector is based on the periodic burning of a gas compound that continuously passes through the pulsed-flame photometric detector. An illustrative, but nonlimiting, example of pulsed-flame photometric detector is disclosed in U.S. Pat. No. 5,153,673 that issued on Oct. 6, 1992 to Amirav, which is incorporated herein by reference. The gas compound is a mixture of combustible fuel or gases that typically includes air and hydrogen in a preferred proportion. There is a wire heated by electric current. This heated wire ignites the fuel compound to produce detectable emissions.

A crucial step in the set-up process is to calibrate the gas mixture. This typically requires a trained and experienced operator to set the gas flow rates. The gas flow rates can vary depending on the specific device, multiple design parameters, temperatures for the heated zones, geometry of the combustion chamber, and so forth.

When the self-ignition state is reached, the ignition, propagation and termination cycle is repeated in a pulsed, periodic fashion at a predetermined frequency. This is known as a stable, continuous cycle. The operator typically needs to perform a fine tuning operation to achieve this state. After the initial calibration, a specific compound is placed in the combustion chamber of the pulsed-flame photometric detector to provide the maximum amount of sensitivity and resolution for the operator.

Therefore, this is not only a time consuming process, but a trained and experienced operator is also required. The element of human error is also ever present. The present invention is directed to overcoming one or more of the problems set forth above.

SUMMARY OF INVENTION

In one aspect of this invention, a system for tuning a pulsed-flame photometric detector is disclosed. This system includes a pulsed-flame photometric detector, having an igniter coil, a mechanism for providing electrical power, a controller, a mechanism for providing a carrier gas that is connected to the controller for regulating an amount of carrier gas flow, at least one mechanism for providing at least one combustible fuel that is connected to the controller for regulating an amount of combustible fuel flow, a container and at least one valve mechanism capable of controlling the amount of the carrier gas capable of entering the container that is connected to the controller, wherein at least one first fluid conduit connects the pulsed-flame photometric detector to the at least one valve mechanism and the container to the at least one mechanism for providing a carrier gas and at least one second fluid conduit connects the at least one mechanism for providing at least one combustible fuel and the pulsed-flame photometric detector.

In another aspect of this invention, a method for tuning a pulsed-flame photometric detector is disclosed. This method includes providing a carrier gas within a predetermined gas flow range to the pulsed-flame photometric detector, providing at least one combustible fuel to the pulsed-flame photometric detector, applying voltage to an igniter coil associated with the pulsed-flame photometric detector, verifying that the pulsed-flame photometric detector is pulsing above a lower predetermined frequency and below a higher predetermined frequency, adjusting the gas flow of the at least one combustible fuel to the pulsed-flame photometric detector so that at least one cycle of ignition, propagation and then termination in the pulsed-flame photometric detector, heating a container, enclosing a tuning compound, to a predetermined temperature, allowing the at least one carrier gas to flow within the container, and monitoring a width of sulfur emission signal resulting from the combustion of the tuning compound for the pulsed-flame photometric detector to determine if the width of sulfur emission signal exceeds a predetermined value.

These are merely two of the numerous illustrative aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF DRAWINGS

For a better understanding of the present invention, reference may be made to the accompanying drawings in which.

DETAILED DESCRIPTION

Figure 1:
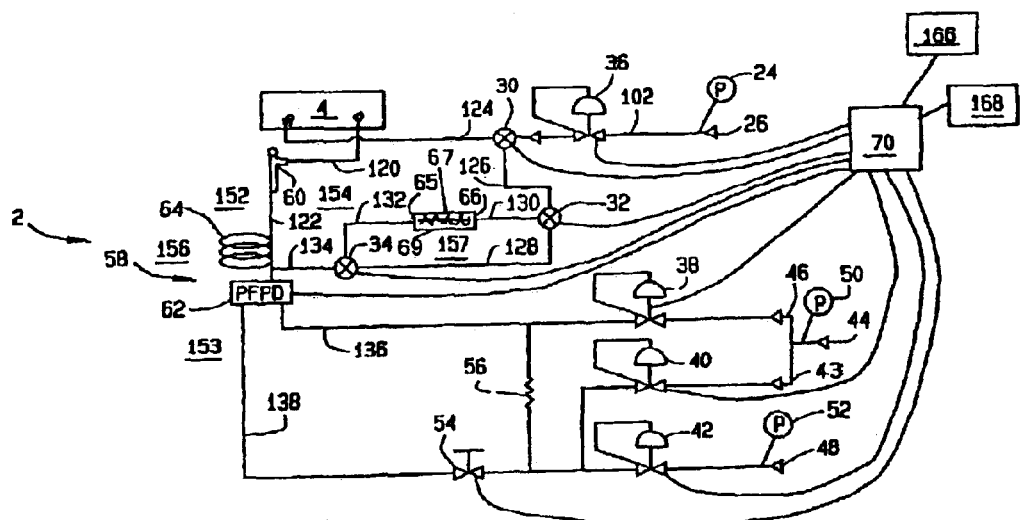
FIG. 1 is a schematic diagram of a preferred embodiment of pulsed-flame photometric detector, which is a component of a low-power gas chromatography

In the following detailed description, numerous specific details are set forth in order to provide a thorough understanding of the invention. However, it will be understood by those skilled in the art that the present invention may be practiced without these specific details. For example, the invention is not limited in scope to the particular type of industry application depicted in the figures, a particular type of software language, or to particular conventions regarding software designations. In other instances, well-known methods, procedures, and components have not been described in detail so as not to obscure the present invention.

Although the present invention can be utilized with virtually any type of pulsed-flame photometric detector, the preferred embodiment is utilized as a component of a low power gas chromatograph that is generally indicated by numeral 2. Referring now to the drawings, and initially to FIG. 1, there is a sample inlet system 4 that can be one or a combination of standard or non-standard gas chromatograph inlet systems such as liquid injection (all types), air collectors (both single air sampling and continuous air sampling), pyrolysis, and so forth. An illustrative, but nonlimiting, example of a sample inlet system 4 can be found in co-pending U.S. patent application Ser. No. 10/248,493 for a Low Power Gas Chromatograph, that was filed Jan. 23, 2003, which is commonly owned by the same assignee as the present patent application.

A first flow controller with flow meter feedback 36 can provide a carrier gas from a carrier gas source 26 and a pressure reducer 24 via a first carrier gas line 102 to a first three (3)-way valve 30. If the a first three (3)-way valve 30 is open, a fluid connection is made between the first three (3)-way valve 30 and the sample inlet system 4 via a second carrier gas line 124. An illustrative, but nonlimiting example of a carrier gas includes helium.

There is a first fluid connector 120 that connects the inlet system 4 with an injector 60. The injector 60 is connected to the gas chromatography column 58 and a pulsed-flame photometric detector 62 via a second fluid connector 122.

The first three (3)-way valve 30 is connected to a second three (3)-way valve 32 via a third fluid connector 126. The second three (3)-way valve 32 is connected to a third three (3)-way valve 34 via a fourth fluid connector 128. The second three (3)-way valve 32 is also connected to a first end portion 66 of a container 67 via a fifth fluid connector 130. A second end portion 65 of the container 67 is connected to the third three (3)-way valve 34 via a sixth fluid connector 132. The third three (3)-way valve 34 is connected to the gas chromatographic column 64 and the pulsed-flame photometric detector 62 via a seventh fluid connector 134.

Combustible fuel is provided to the pulsed-flame photometric detector 62 and may include a combination of hydrogen and oxygen. In the preferred, but nonlimiting example, the pulsed-flame photometric detector 62 is connected to both a third air line 136 and a combination air and hydrogen line 138. The air provided by the third air line 136 is regulated by a second flow controller with flow meter feedback 38 that receives air from a second air line 46. There is a main air supply 44 that provides air, after passing though a second pressure reducer 50, to the second air line 46.

The combination air and hydrogen line 138 is connected to a first end of a fine adjustment valve 54. The second end of the fine adjustment valve 54 is connected to a restrictor tube 56 that connects to the first air line 136. Moreover, the second end of the fine adjustment valve 54 is also connected to a third flow controller with flow meter feedback 40. The third flow controller with flow meter feedback 40 is connected to the first air line 43. The first air line 43, like the second air line 46, receives air from the main air supply 44, after passing though the second pressure reducer 50. Finally, the second end of the fine adjustment valve 54 is also connected to a fourth flow controller with flow meter feedback 42. The fourth flow controller with flow meter feedback 42, receives hydrogen from the hydrogen source 48, after passing through a third pressure reducer 52.

There is a controller 70, which can include virtually any type of processor that is connected to the first three (3)-way valve 30, the second three (3)-way valve 32, the third three (3)-way valve 34, the first flow controller with flow meter feedback 36, the second flow controller with flow meter feedback 38, the third flow controller with flow meter feedback 40, the fourth flow controller with flow meter feedback 42, the pulsed-flame photometric detector 62 and the gas chromatographic column 64. The controller 70 can include one main processor or a series of multiple processors and is preferably programmable.

The operator can provide input to the controller 70 through a wide variety of input devices, a preferred but nonlimiting example includes a keyboard 166. A wide variety of output devices will suffice, with the preferred but nonlimiting example being an electronic display 168, which is a liquid crystal display. Although a liquid crystal display is preferred, cathode ray tube, plasma screen and other types of electronic displays will suffice.

Tuning is accomplished by diverting the carrier gas, e.g., helium, away from the sample inlet system 4 using the first three (3)-way valve 30. The carrier gas, e.g., helium, is sent through the fourth fluid connector 128, which functions as a bypass line, to the pulse-flame photometric detector 62. The container 67 and the third three (3)-way valve 34 are heated to a predetermined temperature, e.g., 200 degrees Celsius to 275 degrees Celsius in a heated zone 157.

The second three (3)-way valve 32 and the third three (3)-way valve 34 are then toggled to their alternative position to allow the carrier gas, e.g., helium, from the carrier gas source 26 to flow through the fifth fluid connector 130 into the first end portion 66 of the container 67, having the tuning compound 69. The carrier gas, e.g., helium, then passes out the second end portion 65 of the container 67 and then into the sixth fluid connector 132. The carrier gas, e.g., helium, then passes through the third three (3)-way valve 34 into the seventh fluid connector 134, which functions as a custom transfer line. The carrier gas, e.g., helium, then passes into the pulsed-flame photometric detector 62. An illustrative, but nonlimiting, flow rate for the carrier gas, e.g., helium is 1.2 milliliters per minute.

The software then adjusts the combustion gas parameters for the pulsed-flame photometric detector 62 according to predefined procedures (described later) to optimize the sulfur emission. When this process is complete, the container 67 is cooled, the second three (3)-way valve 32 and the third three (3)-way valve 34 are then returned to their normal position and the carrier gas, e.g., helium, is returned to the sample inlet system 7 via the first three (3)-way valve 30.

The container 67 preferably, but not necessarily, includes a permeation tube within the container 67 that is sealed at both ends so that no gas flow goes through the permeation tube but rather the gas flow goes around the permeation tube while going through the container 67. The permeation tube is preferably made of TFE (TEFLON®); however, a wide variety of materials will suffice. TEFLON® is a federally registered trademark of E. I. du Pont de Nemours and Company, having a place of business at 1007 Market Street, Wilmington, Del. 19898. An illustrative outer diameter for the permeation tube is 0.3175 centimeters. Preferably, a tuning compound 69 is placed within the container 67. The tuning compound 69 may include any sulfur containing compound with appropriate vapor pressure. However, 1,4 dithiane is the preferred tuning compound 69 and 1,4 thioxane and carbon disulfide are other tuning compounds that may be utilized. The tuning compound 69 will be depleted during multiple tuning operations. Typically, but not necessarily, the permeation tube within container 67 is replaceable.

There are three (3) heated zones that remain at a fixed, predetermined temperature, which are indicated by numerals 152, 153 and 154, respectively. There are also two (2) heated zones that ramp between ambient temperature and a predetermined temperature, which are indicated by numerals 156 and 157, respectively.

The software tuning algorithms are now described herein. In the description of flowcharts, the functional explanation marked with numerals in angle brackets, <nnn>, will refer to the flowchart blocks bearing that number. If during the entire tuning process if a non-fatal error is received, the nonfatal error is logged in an instrument log for the operator and the tuning process is continued. However, if a fatal error is received at any time in the tuning process, the fatal error is logged in an instrument log for the operator and the tuning process is aborted.

Figure 2:
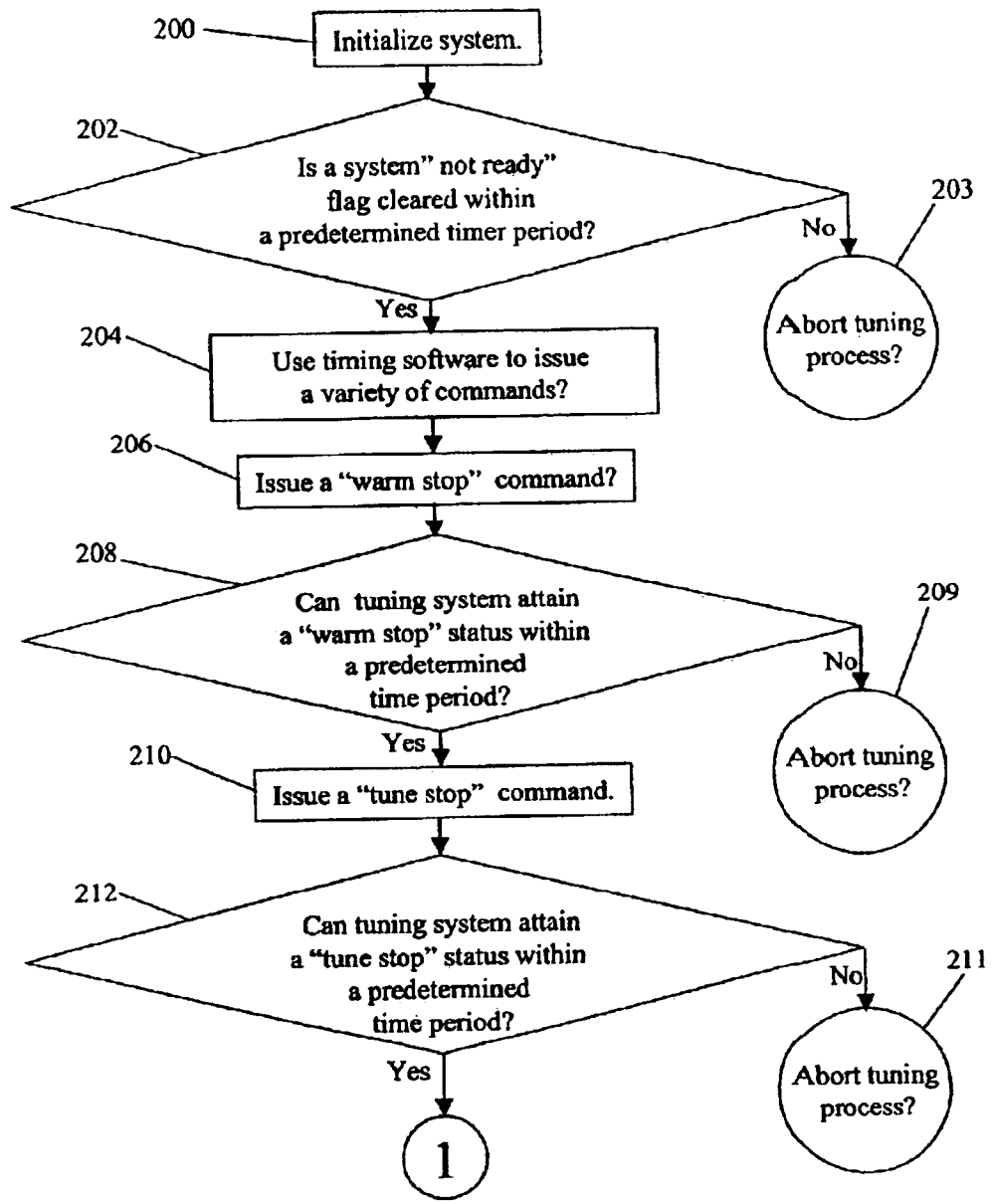
FIGS. 2, 2A, 2B, 2C, 2D, 2E, 2F, 2G, 2H, 2I, and 2J are a flowchart of the process for the self-tuning operation for a pulsed-flame photometric detector associated with the present invention.

Referring now to FIG. 2, the tuning software system is first initialized <200>. The next step is to determine if the system is in a ready state within a predetermined time period, e.g., five (5) minutes. This is preferably accomplished by checking if a not ready flag is cleared within a predetermined time period <202>. If the not ready flag remains in an uncleared state, the tuning process is aborted <203>.

If the not ready flag is cleared in step <202>, there are a number of timing software commands that may be issued <204>. Illustrative examples of these software commands may include: sending signals to receive the status of components associated with the low power gas chromatograph system 2; ensuring the tuning software system is in the expected operating mode; determining the tuning software system status; and determining if tuning software system is not in a ready state and obtaining error flags.

The next step is to issue a warm stop command <206> to attempt place the software system in a warm stop mode. A determination is then made as to whether this warm stop can be achieved within a predetermined time period, e.g., 5 minutes <208>. If warm stop status is unattainable within the predetermined time period, the tuning process is aborted <209>.

If the warm stop mode achieved in step <208>, then the next step is to issue a tune stop command <210> to attempt place the software system in a tune stop mode. A determination is then made as to whether this tune stop can be achieved within a predetermined time period, e.g., 5 minutes <212>. If tune stop status is unattainable within the predetermined time period, the tuning process is aborted <211>.

Figure 2A:
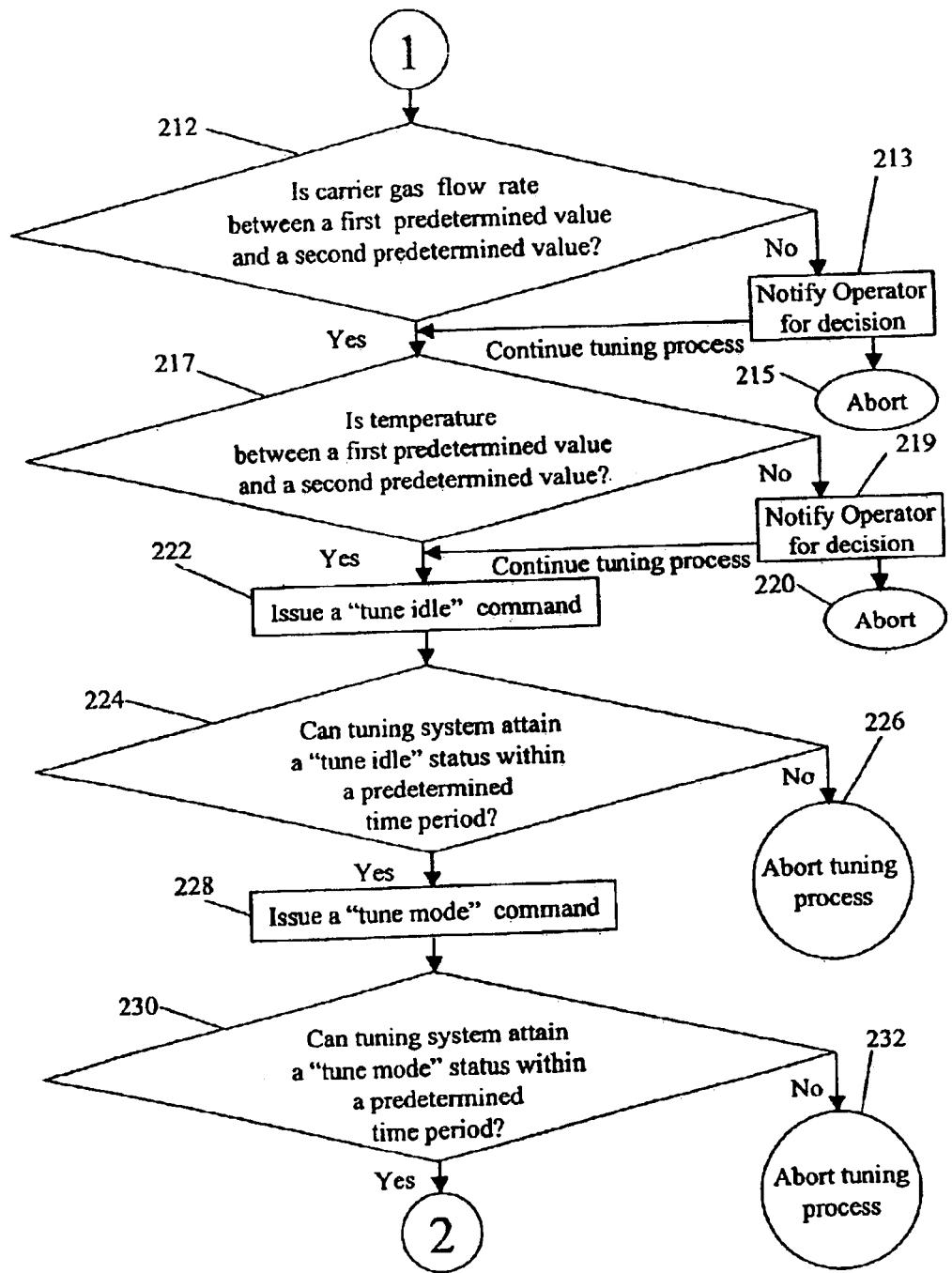

The next step in the tuning process, as shown in FIG. 2A, is to determine if the carrier gas, i.e., helium, flow rate through the first flow controller with flow meter feedback 36, as shown in FIG. 1, is between a first predetermined value, e.g., 1 milliliter per minute, and a second predetermined value, e.g., 1.5 milliliter per minute <212>. If this determination is negative, then the operator is notified in order to make a decision <213>, preferably in a dialog box. The operator can abort the tuning process <215> or allow the tuning process to continue to the next process step after step <212>.

If the carrier gas, i.e., helium, flow rate is between a first predetermined value and a second predetermined value in step <212> or the operator is allowing the tuning process to continue from step <213>, then the next step is to determine if the temperature of the pulsed-flame photometric detector 62, as shown in FIG. 1, is between a first predetermined value, e.g., 200 degrees Celsius, and a second predetermined value, e.g., 275 degrees Celsius <217>. If this determination is negative, then the operator is notified in order to make a decision <219>, preferably in a dialog box. The operator can abort the tuning process <220> or allow the tuning process to continue to the next process step after step <217>.

The next step is to issue a tune idle command <222> to attempt place the software system in a tune idle mode. A determination is then made as to whether this tune idle can be achieved within a predetermined time period, e.g., 5 minutes <224>. If tune idle status is unattainable within the predetermined time period, the tuning process is aborted <226>.

If the tune idle mode achieved in step <224>, then the next step is to issue a tune mode command <228> to attempt place the software system in a tune mode. A determination is then made as to whether this tune mode can be achieved within a predetermined time period, e.g., 5 minutes <230>. If tune mode status is unattainable within the predetermined time period, the tuning process is aborted <232>.

Figure 2B:
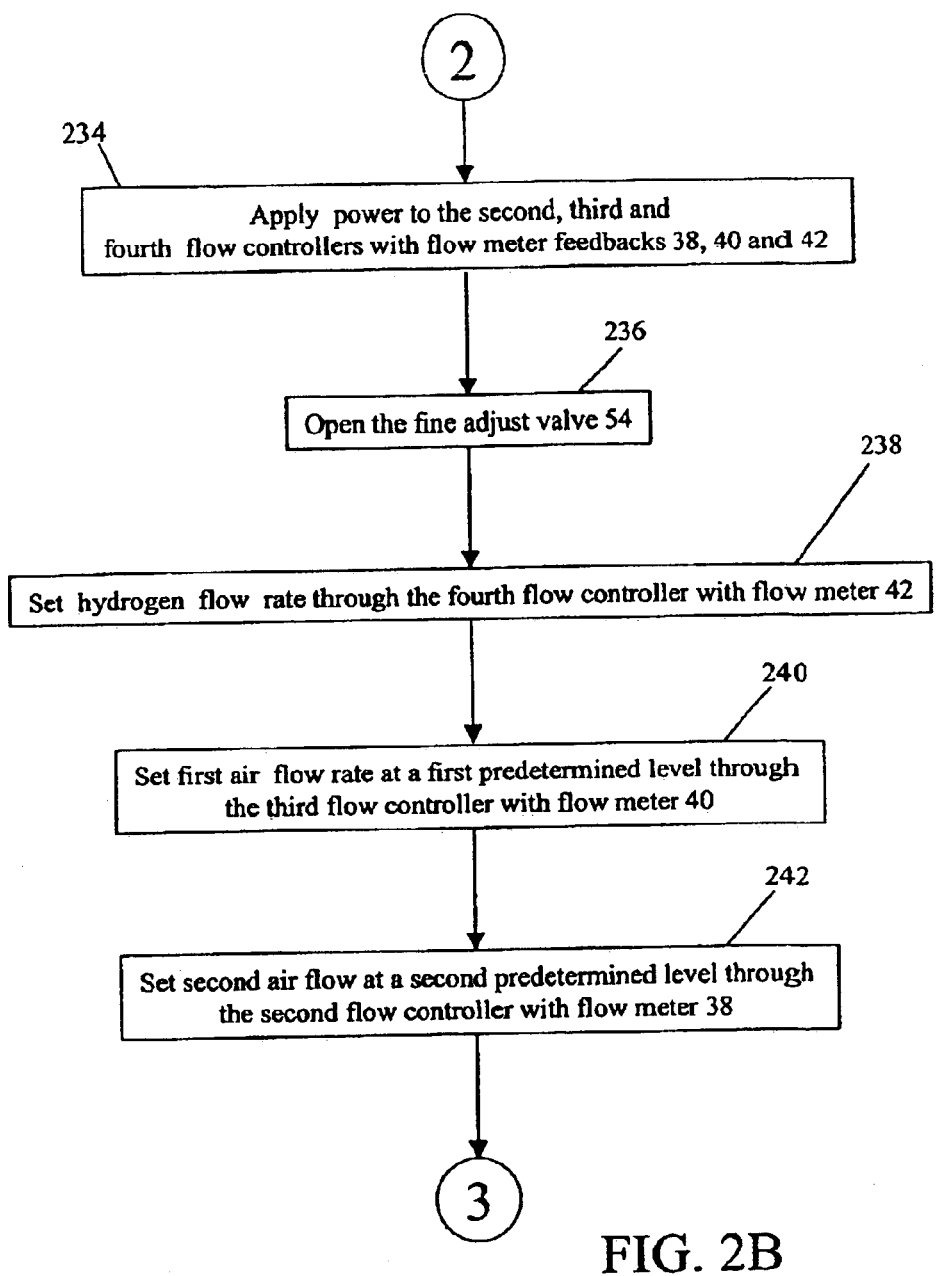

After achieving a tune mode status in step <230>, the next process step in the tuning process, as shown in FIG. 2B, is to issue a command to apply power to the second, third and fourth flow controllers with flow meter feedbacks 38, 40 and 42, as shown in FIG. 1 <234>.

The next step is to open the fine adjust valve 54, as shown in FIG. 1, a predetermined number of turns, e.g., two (2) <236>. Preferably the fine adjust valve 54 is completely closed and an electronic indication is provided of this closed status. The fine adjust valve 54 is preferably opened in increments, e.g., such as twenty (20) one-tenth (1/10) of a turn increments.

A combustible fuel can preferably, but not necessarily, include a hydrogen source 48 and a first air line 43 and a second air line 46. The next step in the process is setting a hydrogen, flow rate <238> at a first predetermined level, e.g., 11.5 milliliters per minute, through the fourth flow controller with flow meter feedback 42, as shown in FIG. 1. This is preferably accomplished through a software command. The next step is to set the first air flow rate at a first predetermined level through the third flow controller with flow meter feedback 40, e.g., 10 milliliters per minute, as shown in FIG. 1 <240>, which is followed by the step of setting a second air flow rate at a second predetermined level, e.g., 15 milliliters per minute, through the second flow controller with flow meter feedback 38 <242>.

Figure 2C:
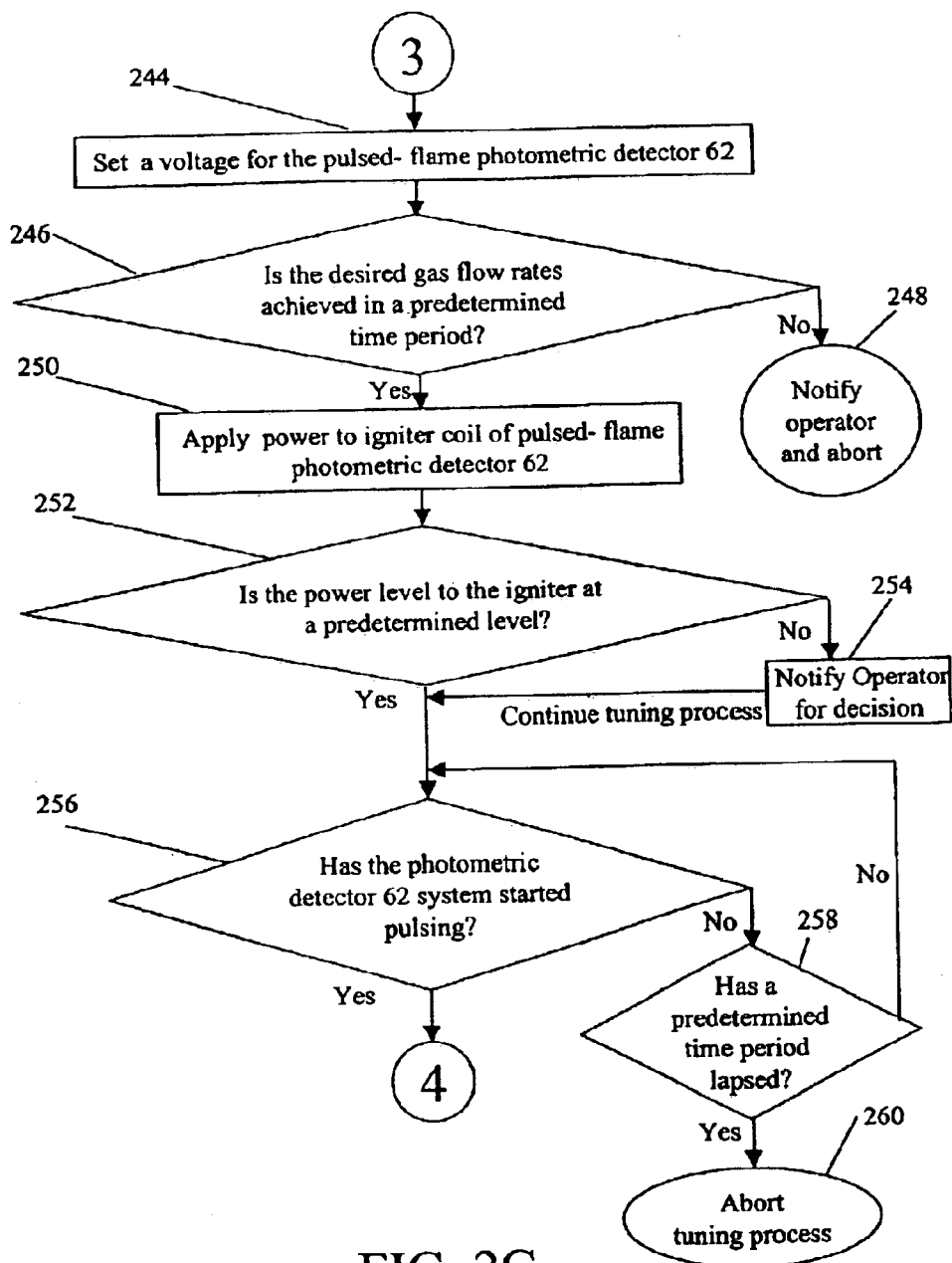

After issuing commands to set the gas flow rates in steps <238>, <240> and <242>, the next step in the tuning process, as shown in FIG. 2C, is to set a voltage, e.g., 10 volts, for the pulsed-flame photometric detector 62, as shown in FIG. 1 <244>. Preferably, this is accomplished by issuing a software command.

The next step <246> in the tuning process is to determine if desired gas flow rates are obtained within a predetermined time period, e.g., two (2) minutes, through the gas flow lines for the second air line 46 from the second flow controller with flow meter feedback 38, for the first air line 43 from the third flow controller with flow meter feedback 40 and from the hydrogen line from the fourth flow controller with flow meter feedback 42 for the combustible gases, as shown in FIG. 1. Preferably, this is accomplished by issuing a software command. If it is not obtained, the tuning software system is aborted and the operator is notified <248>.

If the gas flow is as desired, the next step <250> in the tuning process is to apply power to an igniter coil (not shown) associated with the pulsed-flame photometric detector 62 if it is not already powered. This can be accomplished by issuing a software command. This is followed by determining whether the power applied to the igniter coil is at a predetermined level within a predetermined time period, e.g., two (2) minutes. Preferably, this is accomplished by polling the device status and determining if a status flag is set. If it is not obtained, the operator is notified and can elect to abort or continue the tuning process <254>. This notification may be provided in a dialog box.

The next step in the tuning process, after either determining the power applied to the igniter coil is as desired in step <252> or the operator has elected to proceed in step <254>, is to determine if the pulsed-flame photometric detector 62, as shown in FIG. 1, has started pulsing <256>. If pulsing is not detected, there is a predetermined waiting period to ascertain if pulsing will take place <258>. Preferably, this is accomplished by polling the pulsed-flame photometric detector 62 every predetermined time period, e.g., one (1) second. Therefore, step <256> is repeated until a maximum predetermined period, e.g., thirty (30) seconds, has been reached and then the tuning process <258> is cancelled or aborted.

Figure 2D:
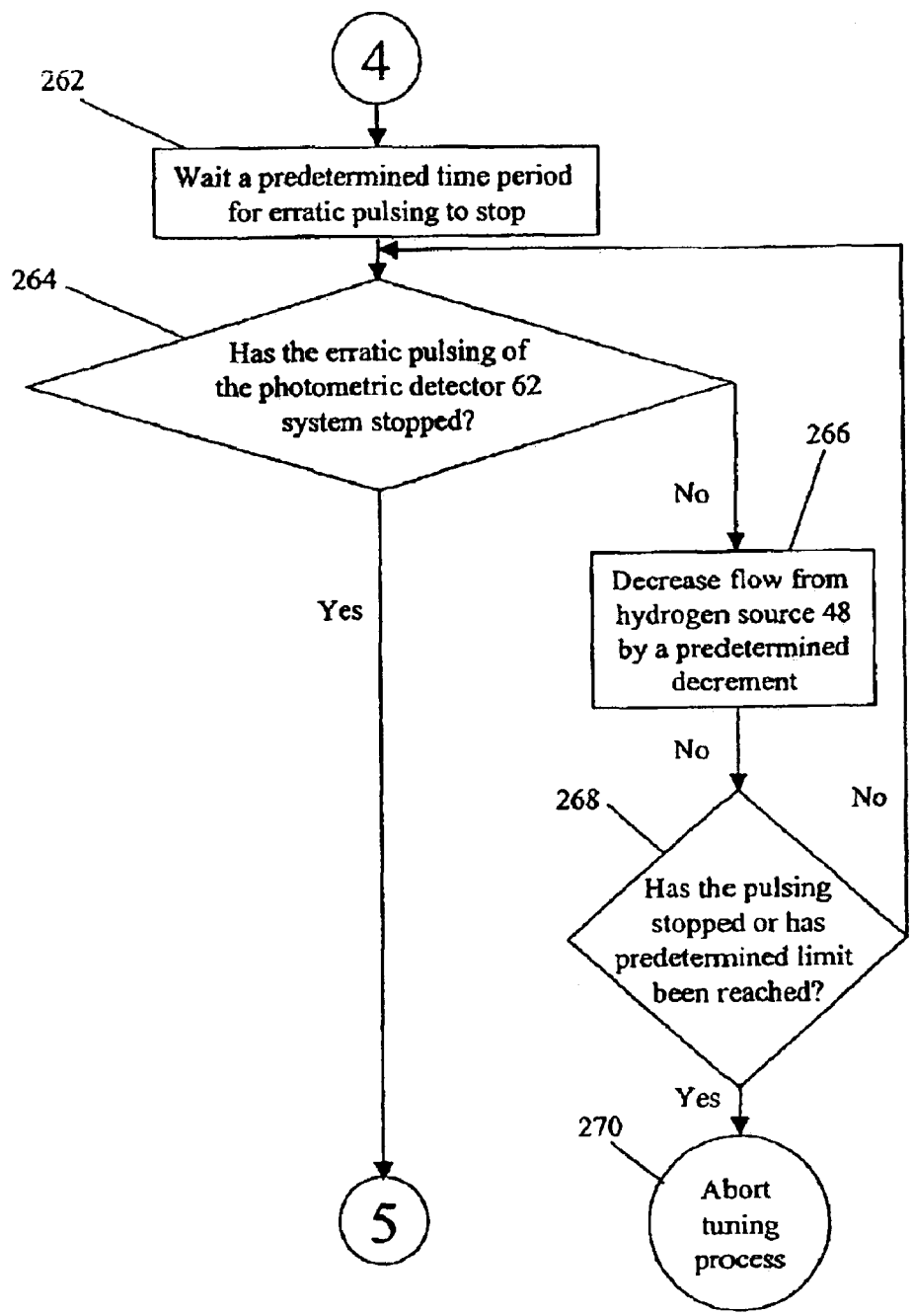

After the pulsing is detected in step <256>, there is a waiting period for a predetermined time period, e.g., thirty (30) seconds, for any erratic pulsing that may be present <262>, as shown in FIG. 2D. A determination is then made if erratic pulsing has subsided <264>. If the response to this query is negative, the hydrogen gas flow is decreased from the fourth flow controller with flow meter feedback 42, as shown in FIG. 1, in a predetermined decremental amount <266>. An illustrative, but nonlimiting, decremental amount includes a reduction is by 0.1 milliliters per minute. A determination is then made if a maximum predetermined change, e.g., 5 milliliters per minute (e.g., 50 steps) has occurred or pulsing has stopped completely <268>. If a response to this determination is positive, the tuning process is then aborted <270>. If tuning has not stopped or the maximum predetermined change has not been reached than process step <264> is repeated.

Figure 2E:
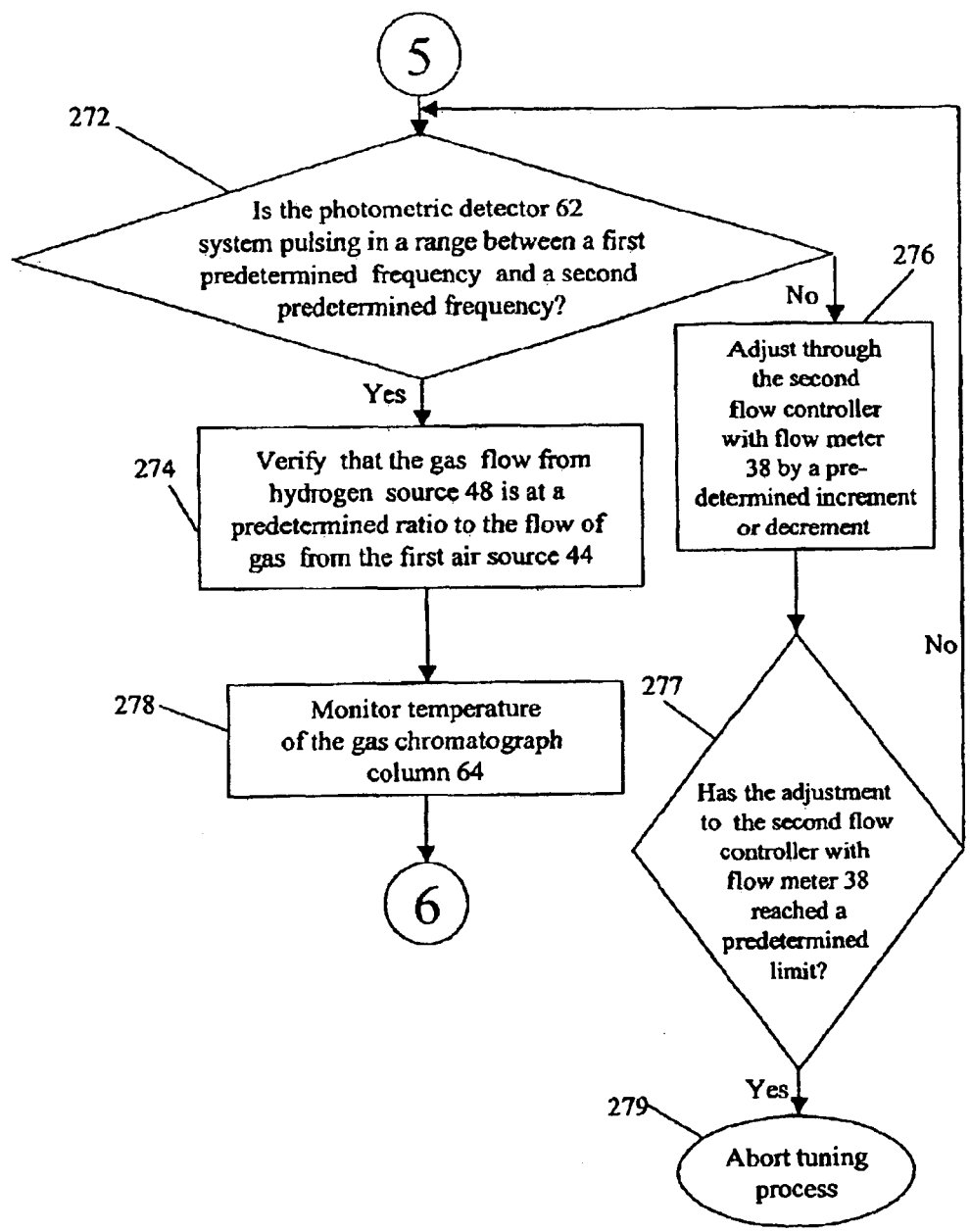

The next step <272> in the tuning process, as shown in FIG. 2E, is to determine if pulsed-flame photometric detector 62, as shown in FIG. 1, is pulsing between a first predetermined frequency, e.g., 3 Hertz, and a second predetermined frequency, e.g., 4 Hertz. This preferably, but not necessarily accomplished, by issuing commands to retrieve error flags, within a predetermined time period, e.g., one (1) second. If this pulsing is between a first predetermined frequency and a second predetermined frequency is not achieved, then the second flow controller with flow meter feedback 38, as shown in FIG. 1, is adjusted so that the airflow is either increased or decreased by a predetermined amount, i.e., increment or decrement <276>. Preferably, this is accomplished by adjusting either upward if the pulse rate is low and downward if the pulse rate is high with software commands during a predetermined time period, e.g., thirty (30) seconds. This can be accomplished in predetermined steps, e.g., 1 milliliter per minute. A determination is then made if a maximum or minimum predetermined value has been reached <277>. If the response to this query is negative, then step <272> is repeated. If the response to this query is positive, then the tuning process is aborted <279>.

If pulsing is occurring between a first predetermined frequency and a second predetermined frequency in step <274>, then the next step in the tuning process is to verify that the gas flow from hydrogen source 48 is at a predetermined ratio to the flow of gas from the first air line 43, as shown in FIG. 1. Preferably, but not necessarily, this can be accomplished with a software command with a predetermined waiting period, e.g., one (1) minute, for this ratio to be achieved. The illustrative, but nonlimiting, ratio is 1.15 to 1.0.

The next step <278> in the tuning process is to monitor the temperature of the gas chromatographic column 64, as shown in FIG. 1, which is followed by the step of allowing the sulfur that is diffused in the gas chromatographic column 64 during a predetermined time period, e.g. five (5) minutes, to stabilize <280>. Temperature is preferably monitored by firmware by creating a contrast with the ambient temperature to determine that the gas chromatographic column 64 will not be damaged by a loss of helium flow.

Figure 2F:
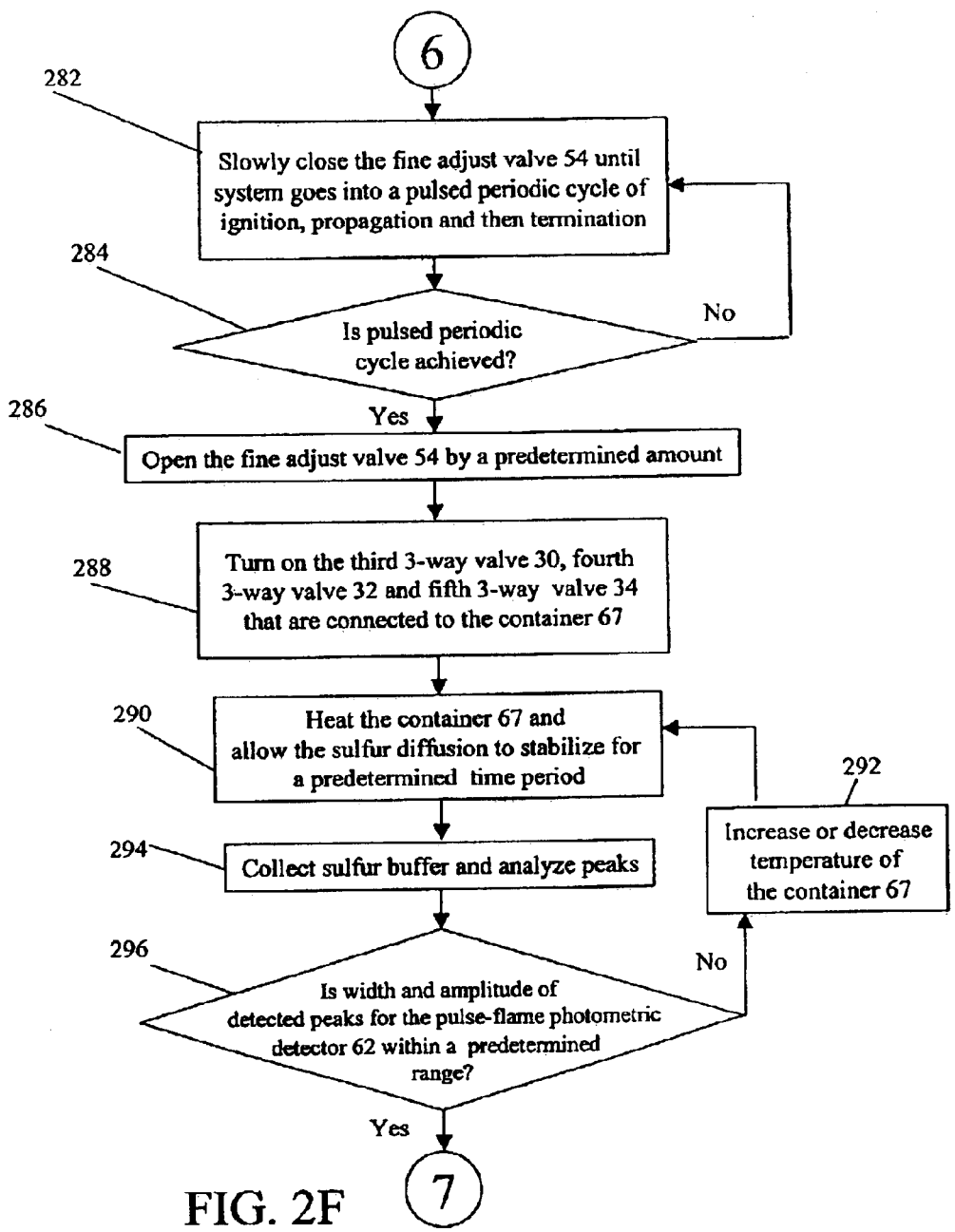

This is followed by slowly closing the fine adjust valve 54, as shown in FIG. 1, until there is an irregular periodic cycle of ignition, propagation and then termination, which is otherwise know as tic-tock. <282>, as shown in FIG. 2F.

The next step <284> in the tuning process is to determine if the tuning process as achieved the pulsed periodic cycle of ignition, propagation and then termination. This is otherwise known as tic-tock. This is preferably, but not necessarily achieved, by recognizing a significant alternating change every other pulse. If the pulsed periodic cycle of ignition, propagation and then termination is not achieved, the tuning process returns to step <282>.

After achieving the irregular periodic cycle of ignition, propagation and then termination, then the fine adjust valve 54, as shown in FIG. 1, is opened by a predetermined amount, e.g., one-half of a turn <286>.

The next step <288> in the tuning process to open the third three (3)-way valve 30, the fourth three (3)-way valve 32 and fifth three (3)-way valve 34 that are connected to the container 67, as shown in FIG. 1. Preferably, but not necessarily, this is accomplished by issuing at least one software command.

The next step <290> in the tuning process is to heat the container 67 at a predetermined temperature, e.g., 100 degrees Celsius, as shown in FIG. 1. Preferably, but not necessarily, this is accomplished by issuing a software command. This is then followed by allowing the sulfur diffusion to stabilize for a predetermined time period, e.g., five (5) minutes after temperature stabilization and sulfur emission.

The tuning compound 69 within the container 67 provides a sulfur source and the sulfur emission signals or peaks are then detected <294>. The next step <296> in the tuning process is to determine if the width and the amplitude of detected sulfur emission signals or peaks for the pulsed-flame photometric detector 62, as shown in FIG. 1, is within a predetermined range. Preferably, but not necessarily, an illustrative value for the width of detected sulfur emission signals or peaks is between a lower predetermined percentage, e.g., 10% (4 milliseconds) and a higher predetermined percentage, e.g., 90% (24 milliseconds). Moreover, preferably but not necessarily, an illustrative value for the amplitude or peak height of detected sulfur emission signals is between a lower predetermined percentage, e.g., 10% (0.75 volts) and a higher predetermined percentage, e.g., 90% (9.0 volts). Preferably, but not necessarily, the fluctuations vary by no more than twenty (20%) percent.

The next step <292> in the tuning process is if the predetermined range of width of detected sulfur emission signals or peaks for the pulsed-flame photometric detector 62, as shown in FIG. 1, cannot be attained, then the temperature of the container 67 is either increased or decreased. The tuning process then returns to step <290>.

Figure 2G:
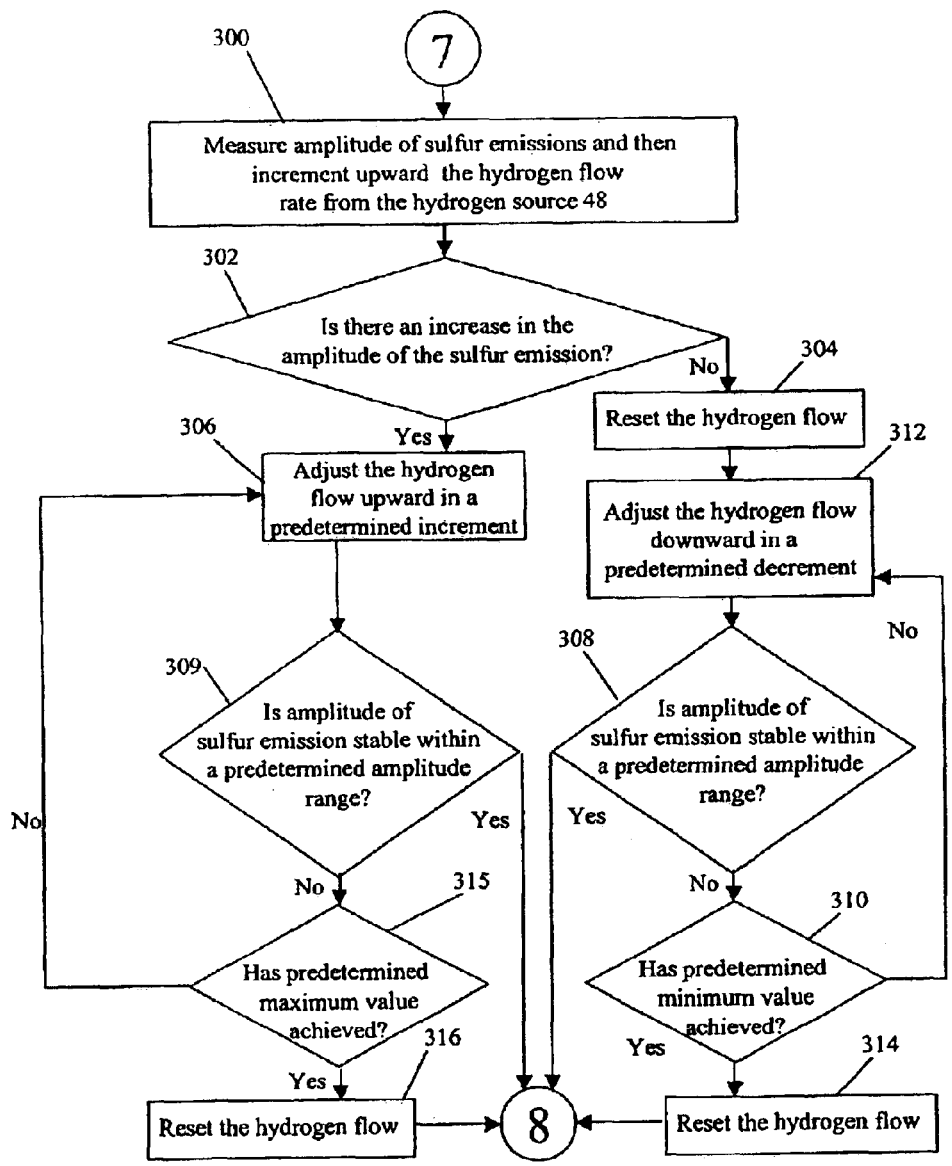

The next step <300> in the tuning process, as shown in FIG. 2G, is to measure the amplitude of sulfur emissions and increment the gas flow upward from the hydrogen source 48. This is followed by a determination as to whether the amplitude of the sulfur emissions has increased <302>.

If the determination in step <302> is affirmative, then the next step in the tuning software process <306> is to keep adjusting the hydrogen flow upward in predetermined increments. This is preferably, but not necessarily accomplished, with software commands. These predetermined increments may preferably, but not necessarily, be in 0.1 milliliter increments. An illustrative, but nonlimiting, starting flow rate may be 11.5 milliliters per minute and the upper rate may be 13.5 milliliters per minute. There is then a determination made as to whether or not the amplitude of the sulfur emissions is at a predetermined value <309>. If the answer to this query is negative, a determination is then made if a predetermined maximum flow value has been achieved <315>. If the answer to this query is negative so that the predetermined maximum flow value has not been achieved, the tuning process goes back to step <306> until the response to the query is positive. If the answer to this query is initially positive so that the predetermined maximum flow value has been achieved, the hydrogen flow is reset <316>.

If the determination in step <302> is negative, then the next step <304> in the tuning process is to reset the hydrogen flow <304> and then decrease the hydrogen flow from the hydrogen source 48 through the fourth flow controller with flow meter feedback 42 in predetermined decrements <312>. This can be accomplished with a software command. These predetermined decrements may preferably, but not necessarily, be in 0.1 milliliter decrements. An illustrative, but nonlimiting, starting flow rate may be 11.5 milliliters per minute and the lower rate may be 9.5 milliliters per minute. There is then a determination made as to whether or not the amplitude of the sulfur emission is at a predetermined value <308>. A determination is then made if a minimum flow value has been achieved <310>. If the answer to this query is negative, the tuning process goes back to step <312> until the response to the query is positive. If the response to the query in step <310> is initially positive, then the hydrogen flow is reset <314>.

Figure 2H:
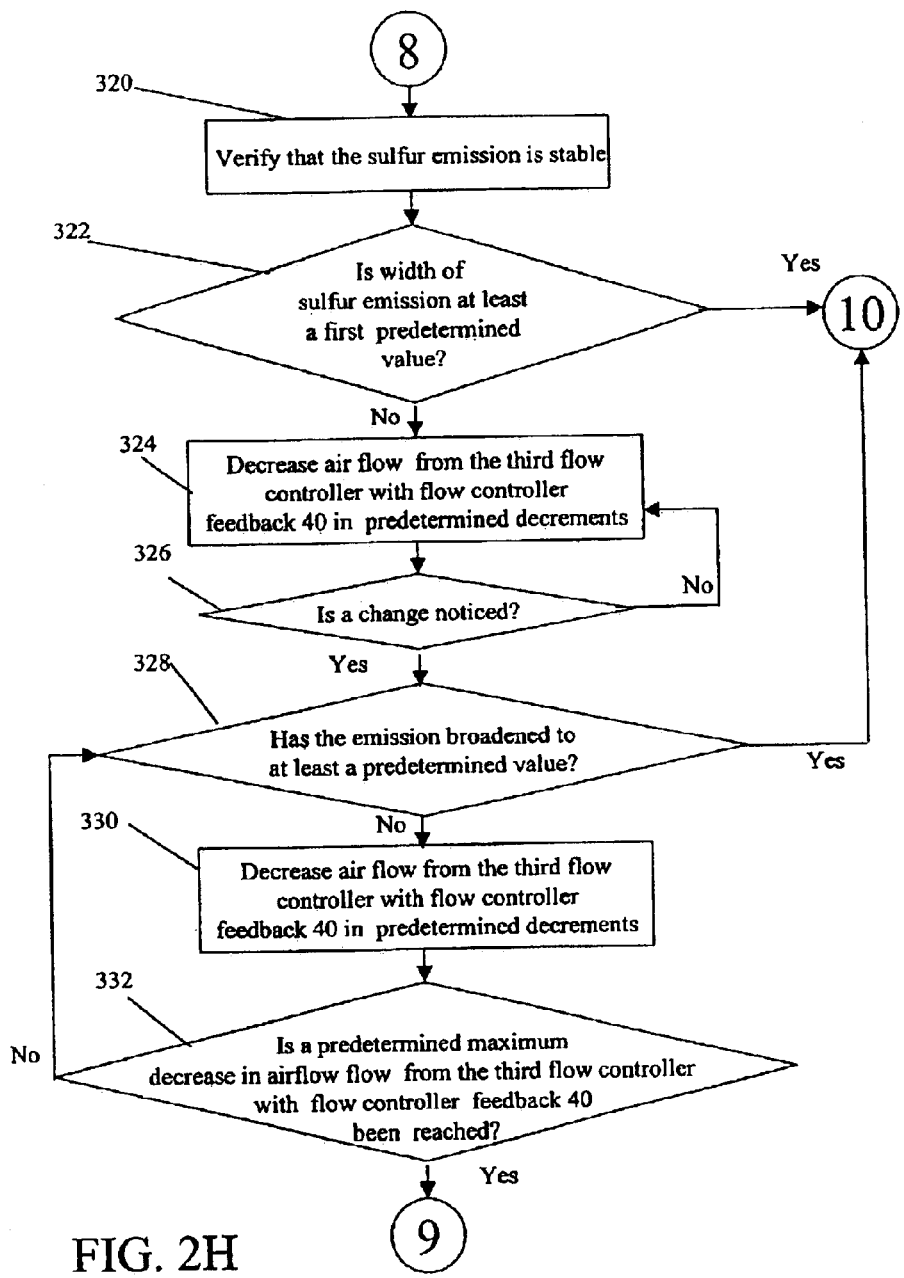

The next step <320>, as shown in FIG. 2H, in the tuning process after either step <309>, <308>, <314> or step <316> is to verify that the sulfur emission is stable by checking that the sulfur emission signals or peaks are within a predetermined percentage of average, e.g., twenty (20) percent. This is then evaluated over a predetermined time period, e.g., ten (10) seconds.

Once the sulfur emission is stable in step <320>, there is a determination as to whether or not the width of the sulfur emission is at least a first predetermined value, e.g., 21 to 24 milliseconds <322>. If the response to this query is negative, then the airflow from the third flow controller with flow meter feedback 40 is decreased in predetermined decrements, e.g., 0.1 milliliters, during predetermined time period, e.g., thirty (30) seconds, <324>. Preferably, but not necessarily, this is accomplished by issuing a software command.

A query is then made as to whether a change in the sulfur emission signal or peak is noticed <326>. If the response to this query is negative, then step <324> is repeated and if response to this query is positive, then a query is made as to whether the sulfur emission peak or signal is broadened to at least a predetermined value, e.g., 21 to 24 milliseconds <328>. If the response to the query in step <328> is negative, then the airflow from the third flow controller with flow meter feedback 40 is decreased in predetermined decrements, e.g., 0.1 milliliters, during predetermined time period, e.g., thirty (30) seconds <330>.

A query is then made as to whether a predetermined minimum value for the airflow from the third flow controller with flow meter feedback 40 has been reached, e.g., five (5) milliliters per minute <332>. If the response to this query is negative, then step <328> is repeated.

Figure 2I:
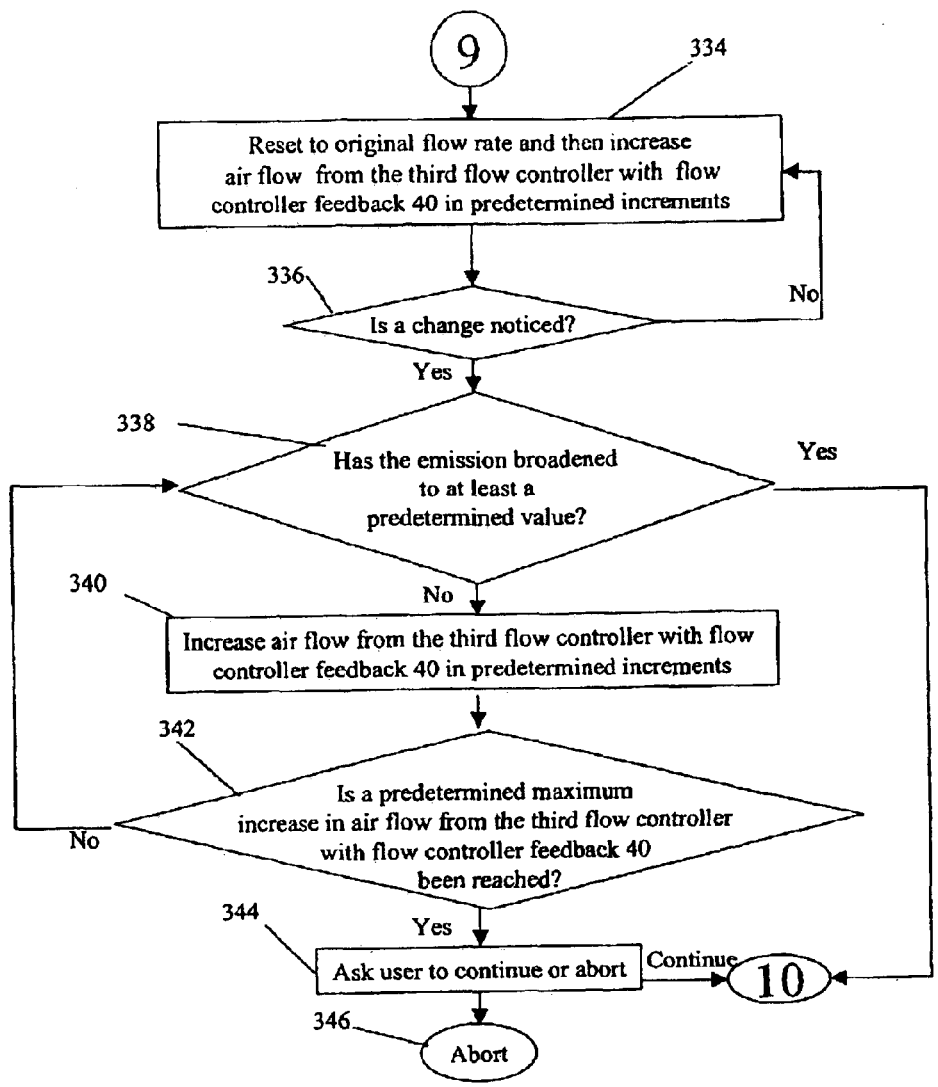

If the response to this query in step <332> is positive, then the airflow from the third flow controller with flow meter feedback 40 is reset and then increased in predetermined increments, e.g., 0.1 milliliters, during predetermined time period, e.g., thirty (30) seconds, which is process step <334> in the tuning process, as shown in FIG. 2I. Preferably, but not necessarily, this is accomplished by issuing a software command. A query is then made as to whether a change in the sulfur emission peak or signal is noticed <336>. If the response to this query is negative, then step <334> is repeated. If the response to the query is positive in step <336>, then a query is made as to whether the sulfur emission peak or signal is broadened to at least a predetermined value, e.g., 21 to 24 milliseconds <338>. If the response to this query is negative, then the airflow from the third flow controller with flow meter feedback 40, as shown in FIG. 1, is increased in predetermined increments, e.g., 0.1 milliliters, during predetermined time period, e.g., thirty (30) seconds <340>.

A query is made as to whether a predetermined maximum value for the airflow from the third flow controller with flow meter feedback 40 has been reached <342>. If the response to this query is negative, then step <338> is repeated and if response to this query is positive, then the operator is presented with the option of either aborting or continuing with the tuning process <344>. Abortion of the tuning process is indicated by step <346>.

Figure 2J:
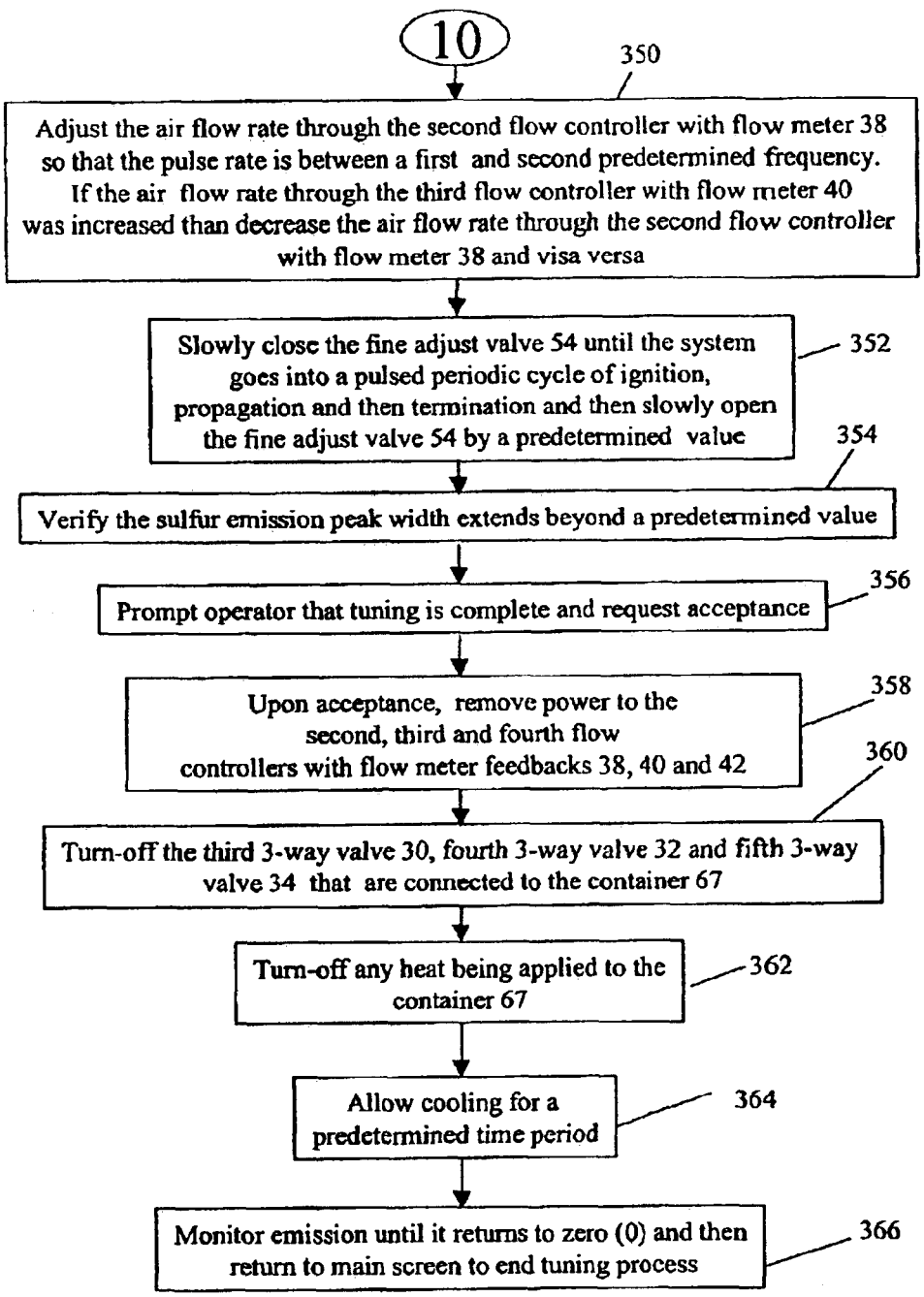

If the response to the query in steps <322>, <328>, <338> and <344> is positive so that the sulfur emission peak or signal is broadened to at least a predetermined value, e.g., 21 to 24 milliseconds, then adjust the airflow rate through the second flow controller with flow meter feedback 38 so that the pulse rate is between a first predetermined frequency, e.g., three (3) Hertz and second predetermined frequency, e.g., four (4) Hertz. If the airflow rate through the third flow controller with flow meter feedback 40 was previously increased than decrease the airflow rate through the second flow controller with flow meter feedback 38 and if the airflow rate through the third flow controller with flow meter feedback 40 was previously decreased than increase the airflow rate through the second flow controller with flow meter feedback 38 <350>, as shown in FIG. 2J.

The next step <352> in the tuning process is to slowly close the fine adjust valve 54, as shown in FIG. 1, until the system goes into goes into a pulsed periodic cycle of ignition, propagation and then termination. The fine adjust valve 54 is then slowly opened by a predetermined value, e.g., one-tenth of a turn.

There is then a verification that the sulfur emission peak or signal width extends beyond a predetermined value, e.g., 21 to 24 milliseconds <354>, which is followed by the prompting of the operator that the tuning process is complete and request acceptance <356>.

Upon acceptance by the operator that the tuning process is complete, power to the second, third and fourth flow controllers with flow meter feedbacks 38, 40 and 42 is removed <358>.

The next step in the tuning process is to turn-off the third three (3)-way valve 30, fourth three (3)-way valve 32 and fifth three (3)-way valve 34 that are connected to the container 67, as shown in FIG. 1 <360>, which is followed by turning-off any heat being applied to the container 67 <362>. This is followed by allowing cooling for a predetermined time period <364>. Finally, the last step <366> in the tuning process is to monitor emission until it returns to zero (0) and then return to main display screen 168 to end the tuning process.

Although the preferred embodiment of the present invention and the method of using the same has been described in the foregoing specification with considerable details, it is to be understood that modifications may be made to the invention, which do not exceed the scope of the appended claims and modified forms of the present invention done by others skilled in the art to which the invention pertains will be considered infringements of this invention when those modified forms fall within the claimed scope of this invention.

What is claimed is:

1. A system for tuning a pulsed-flame photometric detector comprising:
   a pulsed-flame photometric detector, having an igniter coil;
   a mechanism for providing electrical power:
   a controller;
   a mechanism for providing a carrier gas that is connected to the controller for regulating an amount of carrier gas flow;
   at least one mechanism for providing at least one combustible fuel that is connected to the controller for regulating an amount of combustible fuel flow;
   a container; and
   at least one valve mechanism capable of controlling the amount of the carrier gas capable of entering the container that is connected to the controller, wherein at least one first fluid conduit connects the pulsed-flame photometric detector to the at least one valve mechanism and the container to the at least one mechanism for providing a carrier gas and at least one second fluid conduit connects the at least one mechanism for providing at least one combustible fuel and the pulsed-flame photometric detector.

2. The system for tuning a pulsed-flame photometric detector as set forth in claim 1, wherein the container encloses a tuning compound.

3. The system for tuning a pulsed-flame photometric detector as set forth in claim 2, wherein the tuning compound includes a compound containing sulfur.

4. The system for tuning a pulsed-flame photometric detector as set forth in claim 2, wherein the tuning compound is selected from the group consisting of 1,4 dithiane, 1,4 thioxane and carbon disulfide.

5. The system for tuning a pulsed-flame photometric detector as set forth in claim 1, wherein the container includes a permeation tube.

6. The system for tuning a pulsed-flame photometric detector as set forth in claim 5, wherein the permeation tube is removable.

7. The system for tuning a pulsed-flame photometric detector as set forth in claim 1, further includes a gas chromatographic column that connects to the pulsed-flame photometric detector with at least one third fluid conduit, wherein the at least one second fluid conduit and the at least one third fluid conduit are separate until connected to the pulsed-flame photometric detector.

8. The system for tuning a pulsed-flame photometric detector as set forth in claim 1, wherein the container includes a first opening and a second opening and at least one valve mechanism capable of controlling the amount of the carrier gas capable of entering the container includes a first valve controlling carrier gas flow for the first opening of the container and a second valve controlling carrier gas flow for the second opening of the container.

9. The system for tuning a pulsed-flame photometric detector as set forth in claim 8, wherein the first valve includes a first three (3)-way valve and the second valve includes a second three (3)-way valve.

10. The system for tuning a pulsed-flame photometric detector as set forth in claim 1, wherein the pulsed-flame photometric detector includes a first heating mechanism connected to the controller and connected to the mechanism for providing electrical power, wherein the first heating mechanism can selectively control the pulsed-flame photometric detector's temperature.

11. The system for tuning a pulsed-flame photometric detector as set forth in claim 1, wherein the container includes a second heating mechanism that is connected to the controller and to the mechanism for providing electrical power, wherein the second heating mechanism can selectively control the container's temperature.

12. The system for tuning a pulsed-flame photometric detector as set forth in claim 1, wherein the igniter coil for the pulsed-flame photometric detector is connected to the controller and is connected to the mechanism for providing electrical power, wherein the igniter coil can ignite the at least one combustible fuel.

13. The system for tuning a pulsed-flame photometric detector as set forth in claim 1, wherein at least one mechanism for providing at least one combustible fuel that is connected to the controller for regulating the amount of combustible fuel flow includes at least one a flow controller with a flow meter feedback, which is connected to the controller.

14. The system for tuning a pulsed-flame photometric detector as set forth in claim 1, wherein at least one mechanism for providing at least one combustible fuel that is connected to the controller for regulating the amount of combustible fuel flow includes a first flow controller with a flow meter feedback that is connected to a mechanism to provide hydrogen from a hydrogen source, a second flow controller with a flow meter feedback that is connected to a mechanism to provide air from an air source and a third flow controller with a flow meter feedback that is connected to a mechanism to provide air from the air source.

15. The system for tuning a pulsed-flame photometric detector as set forth in claim 1, wherein at least one mechanism for providing at least one combustible fuel that is connected to the controller for regulating the amount of combustible gas flow includes a fine adjust valve for creating at least one cycle of ignition, propagation and then termination in the pulsed-flame photometric detector.

16. The system for tuning a pulsed-flame photometric detector as set forth in claim 1, wherein the controller can ascertain an amplitude of detected sulfur emission signals generated in the pulsed-flame photometric detector to determine if the amplitude is above a lower predetermined value and below an upper predetermined value.

17. The system for tuning a pulsed-flame photometric detector as set forth in claim 1, wherein the controller can ascertain a width of detected sulfur emission signals generated in the pulsed-flame photometric detector to determine if a predetermined width value is exceeded.

18. The system for tuning a pulsed-flame photometric detector set forth in claim 1, wherein at least one mechanism for providing at least one combustible fuel that is connected to the controller for regulating the amount of combustible gas flow includes a first flow controller with a flow meter feedback that is connected to a mechanism to provide hydrogen from a hydrogen source, a second flow controller with a flow meter feedback that is connected to a mechanism to provide air from an air source and a third flow controller with a flow meter feedback that is connected to a mechanism to provide air from the air source, wherein the controller is able to decrease the airflow from the second flow controller with a flow meter feedback in predetermined decrements until the controller can ascertain a width of detected sulfur emission signals generated in the pulsed-flame photometric detector that exceeds a predetermined value for width.

19. The system for tuning a pulsed-flame photometric detector as set forth in claim 18, wherein the controller is able to reset the airflow from the a second flow controller with a flow meter feedback and then increase the airflow from a second flow controller with a flow meter feedback in predetermined increments until the controller can ascertain a width of detected sulfur emission signals generated in the pulsed-flame photometric detector that exceeds a predetermined value for width.

20. The system for tuning a pulsed-flame photometric detector as set forth in claim 1, wherein the container includes a second heating mechanism that is connected to the controller and to the mechanism for providing electrical power, wherein the second heating mechanism can selectively control the container's temperature and wherein the at least one valve mechanism capable of controlling the amount of the carrier gas capable of entering the container and the pulsed-flame photometric detector, wherein the least one valve mechanism and at least one first fluid conduit are heated by the second heating mechanism.

21. A method for tuning a pulsed-flame photometric detector comprising:
  providing a carrier gas within a predetermined gas flow range to the pulsed-flame photometric detector;
  providing at least one combustible fuel to the pulsed-flame photometric detector;
  applying voltage to an igniter coil associated with the pulsed-flame photometric detector;
  verifying that the pulsed-flame photometric detector is pulsing above a lower predetermined frequency and below a higher predetermined frequency;
  adjusting the gas flow of the at least one combustible fuel to the pulsed-flame photometric detector so that at least one cycle of ignition, propagation and then termination in the pulsed-flame photometric detector;
  heating a container to a predetermined temperature;
  allowing the at least one carrier gas to flow within the container; and
  monitoring a width of sulfur emission signal for the pulsed-flame photometric detector to determine if the width of sulfur emission signal exceeds a predetermined value.

22. The method for tuning a pulsed-flame photometric detector as set forth in claim 21, wherein the container encloses a tuning compound.

23. The method for tuning a pulsed-flame photometric detector as set forth in claim 22, wherein the tuning compound contains sulfur.

24. The method for tuning a pulsed-flame photometric detector as set forth in claim 22, wherein the tuning compound is selected from the group consisting of 1,4 dithiane, 1,4 thioxane and carbon disulfide.

25. The method for tuning a pulsed-flame photometric detector as set forth in claim 21, further comprising after the step of allowing the at least one carrier gas to flow within the container and then into the pulsed-flame, photometric detector, monitoring the amplitude of the sulfur emission signal between a first predetermined value and a second predetermined value.

26. A method for tuning a pulsed-flame photometric detector comprising:
  providing a carrier gas at a first predetermined gas flow rate to the pulsed-flame photometric detector;
  providing hydrogen at a second predetermined gas flow rate to the pulsed-flame photometric detector;
  providing a first air stream at a third predetermined gas flow rate to the pulsed-flame photometric detector;
  providing a second air stream at a fourth predetermined gas flow to the pulsed-flame photometric detector within a predetermined range;
  applying voltage to an igniter coil associated with the pulsed-flame photometric detector;
  verifying that the pulsed-flame photometric detector is pulsing above a lower predetermined frequency and below a higher predetermined frequency during a predetermined time period;
  adjusting the flow of hydrogen and the first flow of air to the pulsed-flame photometric detector so that there are a plurality of cycles of ignition, propagation and then termination in the pulsed-flame photometric detector;
  heating a container, enclosing a tuning compound, to a predetermined temperature;
  providing the carrier gas to flow within the container and then to the pulsed-flame photometric detector; and
  monitoring a width of a sulfur emission signal, resulting from combustion of the tuning compound, for the pulsed-flame photometric detector to determine if the width of sulfur emission signal exceeds a predetermined value.

27. The method for tuning a pulsed-flame photometric detector as set forth in claim 26, wherein the tuning compound includes a compound containing sulfur.

28. The method for tuning a pulsed-flame photometric detector as set forth in claim 26, wherein the tuning compound is selected from the group consisting of 1,4 dithiane, 1,4 thioxane and carbon disulfide.

29. The method for tuning a pulsed-flame photometric detector as set forth in claim 26, further comprising adjusting the fourth gas flow rate for the second air stream if the pulsing of the pulsed-flame photometric detector is not above a lower predetermined frequency and below a higher predetermined frequency during a predetermined time period.

30. The method for tuning a pulsed-flame photometric detector as set forth in claim 29, further comprising verifying that a ratio of the a second predetermined gas flow rate for the hydrogen to the third predetermined gas flow rate for the first air stream is within a predetermined range.

31. The method for tuning a pulsed-flame photometric detector as set forth in claim 26, wherein the step of adjusting the flow of hydrogen and the first flow of air to the pulsed-flame photometric detector so that there are a plurality of cycles of ignition, propagation and then termination in the pulsed-flame photometric detector includes utilizing a fine adjust valve.

32. The method for tuning a pulsed-flame photometric detector as set forth in claim 26, further includes verifying the detected sulfur emission signals are stable followed by ascertaining whether an amplitude of detected sulfur emission signals generated in the pulsed-flame photometric detector is above a lower predetermined value and below an upper predetermined value prior to determining a width of a sulfur emission signal for the pulsed-flame photometric detector to determine if the width of sulfur emission signal exceeds a predetermined value.

33. The method for tuning a pulsed-flame photometric detector as set forth in claim 26, wherein the step of monitoring a width of a sulfur emission signal for the pulsed-flame photometric detector determines that the width of sulfur emission signal does not exceed a predetermined value, then decreasing the first air stream at a third predetermined gas flow rate the flow at predetermined decrements over a predetermined time interval until the width of the sulfur emission signal does exceed a predetermined value or a predetermined minimum gas flow rate is achieved.

34. The method for tuning a pulsed-flame photometric detector as set forth in claim 33, wherein the step of adjusting the flow of hydrogen and the first flow of air to the pulsed-flame photometric detector so that there are a plurality of cycles of ignition, propagation and then termination in the pulsed-flame photometric detector includes utilizing a fine adjust valve.

35. The method for tuning a pulsed-flame photometric detector as set forth in claim 31, further includes resetting the first air stream to the third predetermined gas flow rate and then increasing a gas flow rate for the first air stream at predetermined increments over a predetermined time interval until the width of the sulfur emission signal does exceed a predetermined value or a predetermined maximum gas flow rate is achieved.

36. The method for tuning a pulsed-flame photometric detector as set forth in claim 35, wherein the step of adjusting the flow of hydrogen and the first flow of air to the pulsed-flame photometric detector so that there are a plurality of cycles of ignition, propagation and then termination in the pulsed-flame photometric detector includes utilizing a fine adjust valve.

* * * * *